United States Patent [19]

Jacobson et al.

[11] Patent Number: 4,534,967

[45] Date of Patent: Aug. 13, 1985

[54] CELL PROLIFERATION INHIBITOR AND METHOD OF PREPARATION

[75] Inventors: Bernard Jacobson, Lexington; Laurie Raymond, Cambridge, both of Mass.

[73] Assignee: Boston Biomedical Research Institute, Boston, Mass.

[21] Appl. No.: 404,656

[22] Filed: Aug. 3, 1982

[51] Int. Cl.$^3$ ............................................. A61K 35/44
[52] U.S. Cl. ........................................................ 424/95
[58] Field of Search .......................................... 424/95

[56] References Cited

U.S. PATENT DOCUMENTS

| | | | |
|---|---|---|---|
| Re. 30,239 | 5/1984 | Kuettner et al. | 424/95 |
| 3,864,084 | 5/1984 | Folkman | 23/230 |
| 4,042,457 | 5/1984 | Kuettner et al. | 424/95 |
| 4,164,560 | 5/1984 | Folkman et al. | 424/22 |
| 4,176,177 | 5/1984 | Kuettner | 424/95 |
| 4,217,412 | 5/1984 | Tolbert et al. | 435/68 |

OTHER PUBLICATIONS

Guedon et al.—Chem. Abst., vol. 95 (1981) p. 156,572 K.
Raymond et al.—ARVO abst. (Apr. 1980), abst 8-10:15, pp. 145-146.
Jacobson et al.—ARVO abst., (Mar. 1981), abst. 46 p. 216.
"Isolation and Identification of Stimulatory and Inhibitory Cell Growth in Bovine Vitreous", Laurie Raymond and Bernard Jacobson, *Exp. Eye Res.* (Feb. 1982) 34.000–00.

*Primary Examiner*—Sam Rosen
*Attorney, Agent, or Firm*—Weingarten, Schurgin Gagnebin & Hayes

[57] ABSTRACT

An inhibitor of endothelial cell growth is prepared by directly liquifying vitreous gel, as for example, forcing vitreous gel through a small orifice so as to directly convert the gel into a liquid, removing insoluble and suspended material and chromatographically fractionating the liquid and isolating the fractions. An inhibitor is also prepared by culturing hyalocyte cells in a medium and chromatographically fractionating the medium.

14 Claims, 5 Drawing Figures

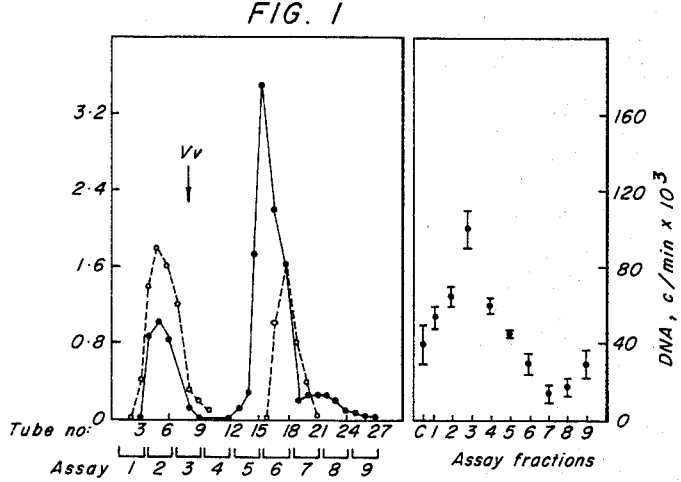

FIG. 1

Bio-Gel P-10 chromatography of bovine vitreous: 25 cc of bovine vitreous was concentrated to 10 cc before loading. Void volume = 24 cc. bed volume = 72 cc. Each fraction represents 2·7 cc. The broken line represents 530 nm absorption and the solid 280 nm absorption.

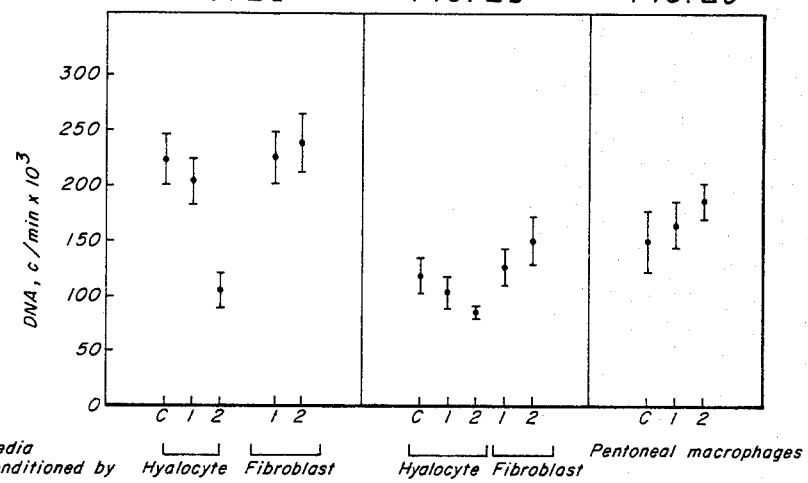

Effect of halyocyte and fibroblast - incubated media on (a) endothelial cells and (b) fibroblasts. Effect of peritoneal macrophage - incubated medium on (c) endothelial cells. C = Control (0·15 M·NaCl in DMEM/NBCS added to wells). 1 and 2 = 1 ml or 2 ml conditioned medium mixed with DMEM/NBCS before addition to wells (see Methods).

CELL PROLIFERATION INHIBITOR AND METHOD OF PREPARATION

The Government has rights in this invention pursuant to Grant No. EY-00810 awarded by the Department of Health and Human Services.

BACKGROUND OF THE INVENTION

This invention relates to a method of preparing an inhibitor of endothelial cell growth. The products of this method are useful in treating or preventing ocular neovascularization and reducing neovascularization in tumors.

Endothelial cells are a key component of blood vessels. Proliferation of vascular endothelial cells play an important role in many biological processes. These include wound healing, formation of inflammatory granulation tissue, the organization of thrombi, the healing of large vessel defects and the repopulation of endothelium in grafts. Normal adult vascular endothelium represents a slowly renewing population of cells. However several pathological situations result in abnormal endothelial cell proliferation with the formation of unwanted new blood vessels. This latter process is called "neovascularization".

Neovascularization of ocular tissues is one of the most important clinical problems in opthalmology. In many disease states the various mature vascular beds of the eye grow beyond their normal limits. Diabetes mellitus is responsible for loss of vision in 12% of the total United States blind population and for 20% of the cases of new blindness in adults between the ages of 45 and 74. Retinopathy, the major cause of blindness in diabetics is responsible in about 84% of blind diabetic patients. At some critical point capillary endothelium begins to proliferate. The new retinal vessels may penetrate the internal limiting membrane of the retina and enter the vitreous where devastating hemorrhages may occur, leading to blindness. During the active, proliferative phase of diabetic retinopathy, neovascularization is also accompanied by fibrous tissue formation, which, when connected between the retinal and vitreous surfaces, can produce tractional elevation and tearing of the retina with subsequent retinal detachment. In the case of diabetic retinopathy, hemorrhage into the vitreous caused by traction on the new blood vessels is treated by removal of the vitreous. Retinal detachment is also sometimes treated by surgery.

The growth of solid tumors has long been recognized to be dependent on the ability of the tumor to induce the formation of new blood vessels by their hosts. The host blood vessels vascularize the solid tumor and provide it with nutrients which allow continued tumor growth.

One object of this invention is to provide an inhibitor of endothelial cell growth.

Another object of this invention is to provide such an inhibitor which will prevent neovascularization in ocular tissue and solid tumors.

Still another object of this invention is to reduce the need for surgery in diabetic retinopathy.

Further objects and advantages of this invention will be apparent from the description and claims which follow.

SUMMARY OF THE INVENTION

This invention comprises broadly preparing a cell proliferation inhibitor by a non-extractive method from a tissue which has neither a high content of collagen, nor proteoglycans. An example of such tissue is the vitreous body including human and animal vitreous. The inhibitor is isolated directly from the vitreous by chromatography, as for example, liquid chromatography. The chromatography fraction having a molecular weight below 10,000 daltons and more particularly having a molecular weight of about 6,000 daltons has been shown to have a particular marked inhibitory effect on the rate of proliferation of endothelial cells and also smooth muscle cells. Another source of inhibitor comprises hyalocyte cells, which release the inhibitor into culture medium.

The cell proliferation inhibitor of this invention, when administered to ocular tissue by appropriate opthalmalogical procedures, is useful in arresting the neovascularization which accompanies diabetic retinopathy.

Also, the cell proliferation inhibitor of this invention, when implanted in the area of solid tumors, causes the tumors to become dormant or to shrink. It is believed that after application of the inhibitor, the tumors may be more susceptible to conventional chemotherapy or radiotherapy.

DESCRIPTION OF THE DRAWINGS

FIG. 1 is a plot of the elution profile of bovine vitreous on Bio-Gel P-10 and the radioactivity appearing in DNA following incubation of aortic endothelial cells with the column fractions and radioactive thymidine;

FIGS. 2a and 2b are plots of the effect of halyocyte and fibroblast-incubated media on endothelial cells and fibroblasts;

FIG. 2c is a plot of the effect of peritoneal macrophage-incubated medium on endothelial cells.

SPECIFIC EXAMPLES OF INVENTION

EXAMPLE 1

Preparation of Bovine Vitreous

Figure 3:
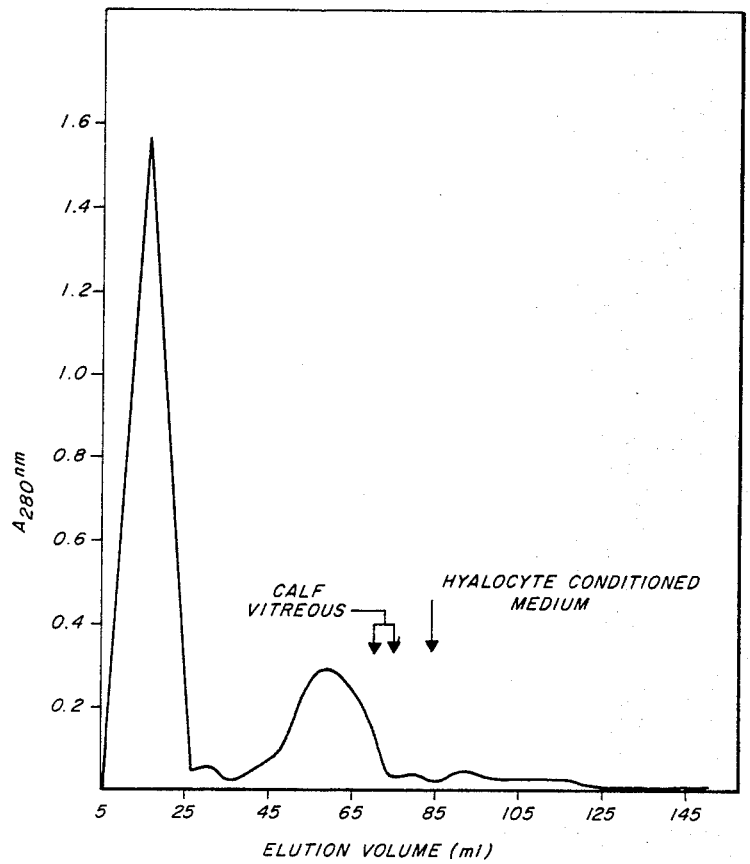
FIG. 3 is a chromatogram of hyalocyte conditioned medium on Bio-Gel P-10.

The posterior portion of the vitreous, which is a clear gel, is removed from bovine eyes. It is then forced through a small orifice (e.g. through a syringe). The resultant material is liquid. The liquid is then centrifuged to remove any tissue debris, cells and the small amount of insoluble collagen. The product may be kept frozen at −20° C., unless used within an 18-hour period, in which case it may be kept at +4° C.

EXAMPLE 2

Liquid Chromatography Fractionation

Bio-Gel P-10 or porous glass beads are preferred. "Bio-Gel P-10" is a commercial polyacrylamide spherical beaded gel sized in particle sizes to permit fractionation in the range of 1,500 to 20,000 daltons. Other suitable media for gel filtration chromatography include ion exchange cellulose chromatography or ion exchange gel chromatography. The vitreous liquid may be concentrated prior to column fractionation by placing it in cellulose tubing of 3,000 dalton cut-off point and covering the tubing with a dry material, such as polyethylene glycol, which draws the water out of the tubing. The vitreous liquid is then loaded onto a chromatographic column containing the Bio-Gel P-10 and eluted with physiological saline, 0.15-M NaCl. The fractions eluted from the column are assayed for ultraviolet absorption at 280 nm. Fractions eluted from the column are mixed with serum-containing tissue culture medium, sterile filtered and added to endothelial cells to test their effect on cell proliferation.

EXAMPLE 3

Endothelial Cell Preparation

Vascular endothelial cells were prepared from calf aorta by the method of Macarak, et al. (Macarak, E. J. Howard, B. V., and Kefalides, N. Lab. Invest. 36, 62-67, [1977]) including treatment of the aortas with a tissue culture medium containing the enzyme collagenase. The endothelial cells were collected in a tissue culture medium e.g. Dulbecco's Modified Eagles Medium (DMEM) containing 10% newborn calf serum (NBCS) plus penicillin, streptomycin and fungizone. The cells were then transferred to culture flasks or dishes and allowed to proliferate in culture medium, and then transferred to 24-well plates for testing of the inhibitory factor. All cell cultures were kept in a humidified $CO_2$ incubator (5% $CO_2$ in air) at 37° C.

EXAMPLE 4

Smooth Muscle Cell Preparation

Smooth muscle cells, grown in the same medium and atmosphere described above, were obtained by the method of Waxler, et al. (Waxler, B., Schumacher, B., and Eisenstein, R. Lab. Invest. 41, 128-134, [1979]), which was modified to include a 75-minute digestion of the media of the aorta with collagenase prior to culture of the cells in culture dishes or flasks. Cells were then trypsinized and added to 24 well plates for subsequent treatment with the cell proliferation inhibitor.

EXAMPLE 5

Fibroblast Cell Preparation

Fibroblasts were obtained from either chick embryos or fetal bovine dermis and grown in the same medium and atmosphere described in Example 3. After allowing the cells to proliferate, they were trypsinized into 24 well plates for subsequent treatment with the cell proliferation inhibitor.

EXAMPLE 6

Assay of Inhibition of Cell Proliferation

The assay procedure was based on cell proliferation being necessarily accompanied by the synthesis of new DNA. One of the constituents of DNA is the nucleoside thymidine. Addition of radioactive thymidine to the cell culture medium results in uptake of radioactive thymidine by the cells and its subsequent incorporation into newly synthesized DNA. A reduction of radioactive thymidine incorporation into newly synthesized DNA is indicative of a reduction in cell proliferation.

Fractions from the column fractionation of vitreous described above were mixed with culture medium in concentrations ranging from 10-40% (V/V), sterile filtered and added in amounts of 0.5 cc per well to duplicate sets of wells already containing the cell type to be tested in 0.5 cc of culture medium. After 24 hours, 0.50 cc were removed from each well and a fresh aliquot of 0.50 cc of the fractions to be tested were added to the wells containing the cells. At the same time, 1 microcurie of radioactive thymidine (tritium-labelled) were also added to each well and the cells allowed to incubate for an additional 24 hours. The culture medium was then removed from the cell layer, the cells briefly washed with fresh culture medium and 0.5 M NaOH added to each well for 8 hours at 37° C. (this treatment extracted DNA from the cells). The contents of each well were transferred to separate test tubes and mixed with non-radioactive DNA (0.5 mg/tube). DNA (mixture of radioactive and non-radioactive) was then precipitated by addition of trichloroacetic acid (final concentration 30%) and collected on 0.45 μm pore size filters. The filters were dissolved in a solvent (e.g. Filtron X) and the radioactive DNA assayed in a liquid scintillation spectrometer. The amount of radioactive DNA in the cells treated with the various column fractions was compared to control cell cultures which received 0.15M NaCl.

EXAMPLE 7

Boiling and Trypsin Treatment of Column Fractions

Those fractions found to have endothelial cell inhibitory capacity were treated in a variety of ways before retesting in a subsequent assay. One portion of each fraction was always left untreated to serve as a control for the other preparations. Aliquots were treated in one of the following ways: (a) boiled at 100° C. for 5 minutes; (b) incubated for two hours at 37° C. with the proteolytic enzyme trypsin. After a 2-hour period, soybean trypsin inhibitor was added in the appropriate ratio for trypsin inhibition to stop the reaction. Controls also included normal saline mixed with trypsin and trypsin inhibitor in an identical manner and an untreated portion, without trypsin or trypsin inhibitor, kept at 37° C. for 2 hours.

FIG. 1 shows, on the left, the elution profile of bovine vitreous on Bio-Gel P-10. On the right is shown the radioactivity appearing in DNA following incubation of aortic endothelial cells with the column fractions and radioactive thymidine. As can be seen, when assay fraction 7 (left hand side of illustration) was added to endothelial cells, a decrease in the radioactivity appearing in DNA (right hand side of illustration) was evident compared to the control level of radioactive DNA ("C" on right side of illustration). The data is expressed as the mean value of the radioactivity from duplicate wells±standard deviation. Table I shows the effect of the vitreous cell proliferation inhibitor on different cell types. The greatest effect was on aortic endothelial cells, with lesser activity towards smooth muscle cells. The effect on fibroblasts is statistically insignificant. Table II shows the effect of boiling and trypsin on the vitreous cell proliferation inhibitor. Destruction of the inhibitory capacity by both boiling and trypsin suggest that the inhibitor is a protein. When the Bio-Gel P-10 column was calibrated using compounds of different molecular weight, the cell proliferation inhibitor was found to be eluted at a position similar to that of 125 I-insulin indicating its molecular weight to be approximately 6,000 daltons. The cell proliferation inhibitor was also found in human post mortem vitreous, following chromatography on Bio-Gel P-10 (pooled fractions 10+11 and 16+17, Table III). In certain cases of diabetic retinopathy the vitreous was surgically removed (vitrectomy). The vitrectomy fluid removing during such an operation also showed fractions with cell proliferation inhibitory capacity following chromatography on Bio-Gel P-10 (fractions 12+13, 22+23, Table IV).

TABLE I

Effect of Vitreous Inhibitory Factor on Different Cell Types

|  | Endothelial | Smooth Muscle | Fibroblasts |
|---|---|---|---|
| Inhibitory factor* | −72.2% | −55.3% | −28.4% |

*Incorporation of $^3H$ thymidine into DNA was measured in duplicate wells for each cell type. Control duplicate wells received medium containing 0.15 M—NaCl. Levels of inhibition were obtained by comparison of the means of each duplicate set of cultures.

TABLE II

Effect of Boiling and Trypsin on Vitreous Inhibitory Factor

|  | DNA (c/min) |
|---|---|
| Control | 42985 ± 4387 |
| Inhibitory factor | 7855 ± 4672 |
| Inhibtory factor (boiled) | 32567 ± 8545 |
| Inhibitory factor (trypsin) | 22487 ± 5643 |

TABLE III

Human Vitreous Inhibitor of Cell Proliferation

| Bio-Gel P-10 Fraction | Percent Inhibition of Thymidine Uptake |
|---|---|
| 10 + 11 | 84.6 |
| 16 + 17 | 48.5 |

Incorporation of ($^3H$)-thymidine into DNA was measured in duplicate wells for each fraction. Control duplicate wells for each fraction received medium containing 0.15 M NaCl. Levels of inhibition were obtained by comparison of the means of each set of duplicate cultures.

TABLE IV

Presence of Inhibitor of Cell Proliferation in Vitrectomy Fluid

| Experiment | Bio-Gel P-10 Fraction | Percent Inhibition of Thymidine Uptake |
|---|---|---|
| 1 | 12 + 13 | 37.4 |
|  | 22 + 23 | 38.8 |
| 2 | 9 + 10 | 42.5 |
|  | 11 + 12 | 48.6 |
|  | 19 + 20 | 13.9 |

Experimental conditions as described in Table 1. In experiment 1, vitrectomy fluid from a 48 year old male diabetic was used. In experiment 2, pooled fluids from the following cases were used: male, 54 years, hemmorrhagic ocular injury; female, 53 years, subdural hemorrhage; male, 68 years, retinal detachment.

EXAMPLE 8

Hyalocyte Cultures

Calf eyes were trimmed of surrounding connective tissue, rinsed in running cold tap water and soaked for 30 minutes in a bactericidal/fungicidal solution (Duet, Madison Bionics). After rinsing the eyes again in distilled $H_2O$, the posterior gel, containing the hyalocytes was isolated essentially as described by Balazs, Toth, Eckl and Mitchel (Exp. Eye Res. 3, 57–81, [1954]). The gel pieces were passed through a syringe (without a needle) to break the gel. The vitreous, containing the hyalocytes, was then incubated with sterile-filtered collagenase (1 mg/cc, Type III, Worthington Biochemical Corp.) and leech hyaluronidase (1 mg/cc, Biomatrix) in Earle's Basal Medium (BME containing Earle's salts [GIBCO], glutamine, 20 mM-Na pyruvate instead of glucose, 20 mM:Hepes, vitamins and Gentamicin, without serum) at 37° C. until inspection showed the vitreous to be significantly reduced in viscosity. At this point, the cells were isolated by centrifugation at 1000 r/min in a Beckman TJ-6 centrifuge for 10 min., suspended in fresh BME and kept for 18 hr. without shaking in humidified 5% $CO_2$ in air. Each separate tube included cells from two eyes. After 18 hours, the cells were separated from the culture medium by centrifugation as described above. The medium was mixed with DMEM/10% NBCS, sterile fitered and added to wells, containing the cells on whose growth the conditioned medium was to be tested, in the range of concentrations and amounts/well described above in Examples 6 and 7. Cell viability of the hyalocytes was well maintained up to at least 18 hours as demonstrated by the cells' 95% exclusion of trypan blue.

Fibroblasts were trypsinized and transferred to wells as described above. When they reached 75% confluence, fresh medium was added for 18 hours. Medium was collected from each well, centrifuged at low speed and the supernatants pooled. The pooled media were mixed, sterile filtered and added to the wells in the range of concentrations and amount/wells described above for hyalocyte-conditioned medium.

Macrophages were obtained from CD-1 strain white male mice (Charles River Breeding Laboratories). Five to eight cubic centimeters of BME/20% NBCS was injected into the peritoneal cavity, circulated by gentle massage and then withdrawn. Three separate washes per mouse were pooled and spun at 1000 r/min for 5 minutes. Cells were resuspended in BME/20% NBCS and transferred to wells. Within 30 minutes, macrophages adhered to the flask surface and remaining unattached cells were removed by vigorously washing three times with the same medium. Subsequent treatment of the cells with 0.025% trypsin 24 hours later removed any remaining fibroblasts after with fresh medium (BME/20% serum) was added for 18 hours. The medium was then isolated and added to wells in the range of concentrations and amounts/well described above for hyalocyte-conditioned medium. The effect of medium conditioned by hyalocytes, fibroblasts and peritoneal macrophages on the growth of aortic endothelial cells is shown in FIGS. 2a and 2c. The effect of medium conditioned by hyalocytes and fibroblasts on the growth of fibroblasts is shown in FIG. 2b. When hyalocyte-conditioned medium is chromatographed on Bio-Gel P-10, the cell growth inhibitor appears in a position similar to that of the inhibitor from bovine vitreous, indicating the close similarity between the two molecules (FIG. 3).

What is claimed is:

1. A non-extractive method for preparing an inhibitor of cell growth, comprising directly liquefying vitreous gel in the absence of extraction solvent by application of shear forces to the gel so as to directly convert the gel into a liquid, removing any insoluble and suspended material from the liquid, chromatographically separating the liquid into fractions of varying molecular weight and isolating a product having inhibitory activity.

2. The method of claim 1 wherein the direct liquefaction is accomplished by forcing the gel through a small orifice.

3. The method of claim 1 wherein the direct liquefaction is accomplished by application of ultrasonic vibration.

4. The method of claim 1 wherein the product inhibits growth of endothelial cells.

5. The method of claim 1 wherein the product inhibits growth of smooth muscle cells.

6. The method of claim 1 wherein the product has a molecular weight of less than approximately 10,000 daltons.

7. The method of claim 1 wherein the product has a molecular weight of approximately 6000 daltons.

8. The method of claim 1 wherein the vitreous gel is of animal origin.

9. The method of claim 1 wherein the vitreous gel is of human origin.

10. The method of claim 1 wherein the liquid is separated into fractions by liquid chromatography utilizing an eluant.

11. The method of claim 10 wherein the eluant is physiological saline.

12. The inhibitor of cell growth made by the method of claim 1.

13. A method of treating or preventing ocular neovascularization comprising the administration to ocular tissue of the inhibitor of claim 12.

14. A method of reducing neovascularization in a tumor comprising the administration to the tumor of the inhibitor of claim 12.

* * * * *

UNITED STATES PATENT AND TRADEMARK OFFICE
CERTIFICATE OF CORRECTION

PATENT NO. : 4,534,967
DATED : August 13, 1985
INVENTOR(S) : Bernard Jacobson; Laurie Raymond It is certified that error appears in the above-identified patent and that said Letters Patent is hereby corrected as shown below:

Column 1, line 16, "play" should read --plays--

Column 4, line 65, "removing" should read --removed--

Column 5, line 40, "hemmorrhagic" should read --hemorrhagic--
line 52, "[1954]" should read --[1964]--
line 60, "mM:Hepes," should read --mM-Hepes,--

Column 6, line 29, "with" should read --which--

Column 8, line 1, "The inhibitor" should read --An inhibitor--

Signed and Sealed this

Fifteenth Day of March, 1988

Attest:

DONALD J. QUIGG

Attesting Officer

Commissioner of Patents and Trademarks